United States Patent
Yung et al.

(10) Patent No.: US 11,353,425 B2
(45) Date of Patent: Jun. 7, 2022

(54) METHOD FOR MEASURING STATIC ATTRACTION PROPENSITY

(71) Applicant: Ascend Performance Materials Operations LLC, Houston, TX (US)

(72) Inventors: Wai-shing Yung, Pensacola, FL (US); Harrie Schoots, League City, TX (US); Rahim Jindani, Houston, TX (US); Victor G. Kholodkov, Pensacola, FL (US); Jeffrey L. Walker, Cantonment, FL (US)

(73) Assignee: Ascend Performance Materials Operations LLC, Houston, TX (US)

( * ) Notice: Subject to any disclaimer, the term of this patent is extended or adjusted under 35 U.S.C. 154(b) by 0 days.

(21) Appl. No.: 16/996,272

(22) Filed: Aug. 18, 2020

(65) Prior Publication Data
US 2021/0055261 A1 Feb. 25, 2021

Related U.S. Application Data

(60) Provisional application No. 62/889,360, filed on Aug. 20, 2019.

(51) Int. Cl.
*G01N 27/60* (2006.01)
(52) U.S. Cl.
CPC .................... *G01N 27/60* (2013.01)
(58) Field of Classification Search
CPC ............................ G01N 27/60; G01N 33/367
USPC ......................................................... 324/452
See application file for complete search history.

(56) References Cited

U.S. PATENT DOCUMENTS

| | | | | |
|---|---|---|---|---|
| 4,403,191 A * | 9/1983 | Satake | ................... | G01N 33/10 324/452 |
| 4,673,885 A * | 6/1987 | Lewiner | ................. | G01R 29/24 361/220 |
| 5,066,918 A * | 11/1991 | Pazda | .................... | G01N 27/60 324/452 |
| 6,730,908 B2 * | 5/2004 | Bigarre | .............. | G01R 27/2617 850/16 |
| 6,888,356 B2 * | 5/2005 | Jean-Raoul | ............. | B07C 5/344 324/452 |

(Continued)

FOREIGN PATENT DOCUMENTS

| | | |
|---|---|---|
| JP | S56114754 A | 9/1981 |
| JP | 2005036354 A | 2/2005 |

(Continued)

OTHER PUBLICATIONS

Folkins, Jeffrey J. "Intermediate conductivities—the crossover function for insulative and conductive two-component magnetic brush development in electrophotography." IEEE Transactions on Industry Applications 24.2 (1988): 250-255. (Year: 1988).*

(Continued)

*Primary Examiner* — Christopher P McAndrew
(74) *Attorney, Agent, or Firm* — Cozen O'Connor

(57) ABSTRACT

A method for measuring the attraction propensity of fabric including the steps of charging a neutralized test fabric, optionally by contacting with a charging fabric, presenting the charged test fabric a predetermined distance from a static-influenced agent such that at least a portion of the static-influenced agent attaches to the charged test fabric, and determining the quantity of attached static-influenced agent.

22 Claims, 1 Drawing Sheet

Attraction Propensity of Charged Fabrics

● Polyester Lint   × Cotton Lint   ▲ Cat Hair   ■ Dog Hair

Various Fabric Compositions, 1 inch Air Gap, Data points are average of 9 tests by 3 operators

(56) References Cited

U.S. PATENT DOCUMENTS

| | | | | |
|---|---|---|---|---|
| 8,198,901 B2* | 6/2012 | Varoon | ............... | G01N 27/60 |
| | | | | 324/452 |
| 2009/0195253 A1* | 8/2009 | Varoon | ............... | G01N 27/60 |
| | | | | 324/457 |
| 2009/0195254 A1* | 8/2009 | Varoon | ............... | G01N 27/60 |
| | | | | 324/457 |
| 2015/0301003 A1* | 10/2015 | Martiska | ............. | G01N 27/60 |
| | | | | 73/866 |
| 2018/0210026 A1* | 7/2018 | Nikic | .................. | G01N 27/61 |

FOREIGN PATENT DOCUMENTS

| | | | |
|---|---|---|---|
| JP | 2010060447 A | | 3/2010 |
| KR | 20160001946 U | | 6/2016 |

OTHER PUBLICATIONS

Holdstock, Paul. "Limitations of using resistance measurements to qualify garments for use in EPA." EOS/ESD 2008—2008 30th Electrical Overstress/Electrostatic Discharge Symposium. IEEE, 2008. (Year: 2008).*

Ireland, Peter M. "Dynamic particle-surface tribocharging: The role of shape and contact mode." Journal of Electrostatics 70.6 (2012): 524-531. (Year: 2012).*

* cited by examiner

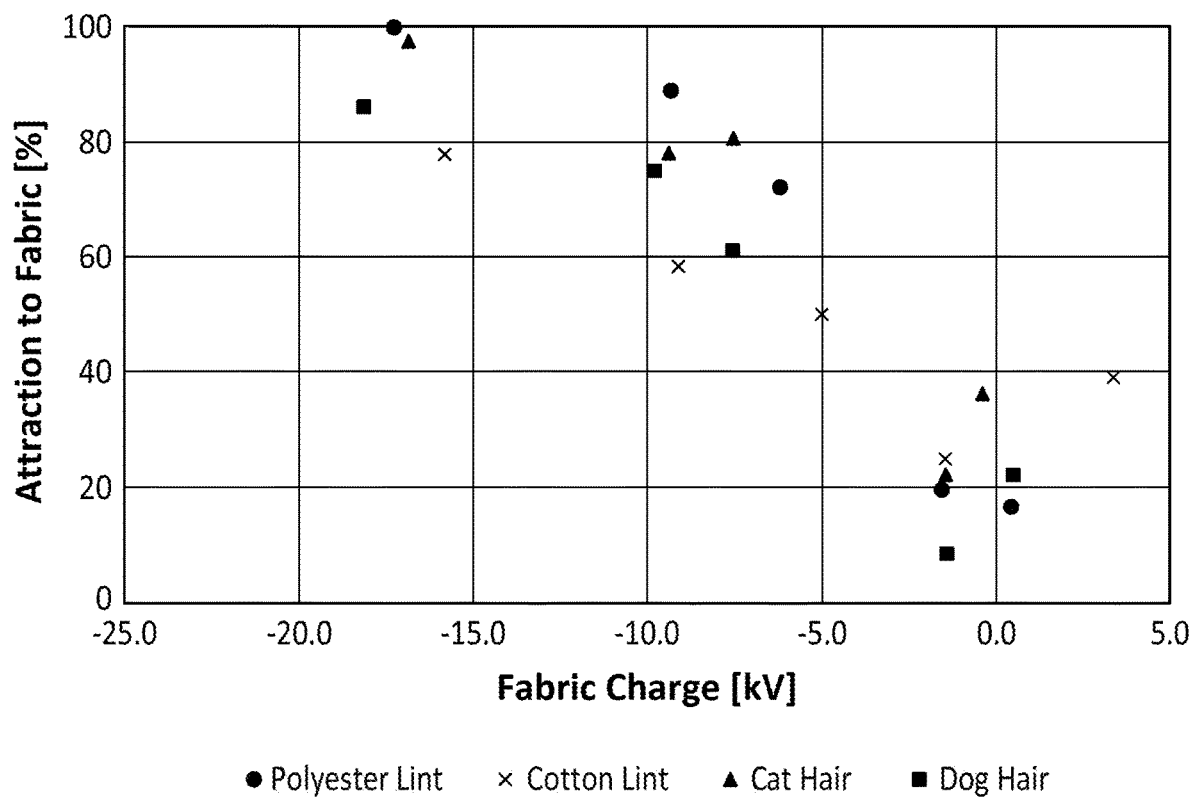

METHOD FOR MEASURING STATIC ATTRACTION PROPENSITY

FIELD

The present disclosure relates generally to the testing of electrostatic properties of fabrics. In particular, the present disclosure relates to a test method for evaluating the static attraction propensity of a fabric and accumulation of a static-influenced agent on the fabric's surface.

BACKGROUND

Conventional fabrics, e.g., clothing, tend to attract and collect various unwanted static-influenced particles, such as lint, hair, or dust due to electrostatic charges between the particles and the fabric. The collection of such particles on clothing has long been deemed a nuisance—consumers generally want their clothes (especially dark clothes) to be free of unsightly lint, hair, or dust. Often it is the static properties of the fabric that lead to the attraction/collection of the lint, dust, or hair. Fabrics generate an electrostatic charge due to the transfer of electrons through contact electrification. Contact electrification refers to the phenomenon wherein electrons transfer from one medium to another during contact and separation, which results in a charge imbalance. Unfortunately, electrostatic (or simply static) buildup is unavoidable with normal daily activities where contact or rubbing of two surfaces, e.g., by one fabric surface rubbing a second fabric surface, occurs frequently. The accumulation of particles on fabric surface generally occurs because of the electrostatic attractive force between the charged fabric and particles polarized by the charged fabric. Particles are polarized, so that the attractive force on the nearer side of the particle is opposite that of the charged fabric. Thus, the polarity of the charge on the polarized particles is always opposite to that of the charged fabric, so the force between the charged fabric and the particles are always attractive and never repulsive in nature. As the attractive force between the charged fabric and the oppositely charged portion of the polarized particle is greater than the repulsive force between the charged fabric and the same charge portion of the polarized particle, the particle is attracted and attaches to the charged fabric, resulting in the particle accumulation.

The extent of charge buildup and the ability for fabrics to dissipate the buildup can be quantitatively measured using various conventional techniques such as measuring the static decay time, actual amount of charge buildup, or the time period a fabric sample would cling to a metal plate. Test Methods or Standards, such as EN1149, Fed Std. 191A-5931, or AATCC TM 115, have been established by various agencies to standardize these measurements.

As different remedies have been developed over time to reduce the impact of static charge, these test methods are essential to evaluate the efficacy of each of these remedies. As an example of one remedy, very thin conductive metal wires or yarn containing conductive carbon have been woven into fabrics to eliminate or reduce static buildup by allowing the imbalanced charge to dissipate rapidly through grounding or corona discharge. Electrically conductive surface treatment can also be applied. Conventional test methods provide for an evaluation of the effectiveness of static charge reduction using these antistatic solutions.

While these methods are good for measuring the ability to dissipate charge, these methods do not provide a quantitative test for determining a fabric's propensity for static attraction (and accumulation) of particles, e.g., a way to gauge how a fabric or garment will behave in the presence of lint, dust, hair, or other static-influenced agents when the garment is electrostatically charged during normal daily activities. Such a metric is primarily of interest to producers and consumers of fabrics and the garments made therefrom. Nor has the correlation between static charge and a fabric's propensity for static attraction been reduced to a quantitative relationship. A fuller understanding of that quantitative relationship would provide a technical means to predict and assess the fabric's propensity for static attraction.

Thus, a need exists for a test method to quantitatively measuring the propensity of a fabric to attract static-influenced agents and to evaluate accumulation of the static-influenced agents on the fabric surface.

SUMMARY

According to one embodiment, the present disclosure relates to a method for measuring the attraction propensity of a fabric, the method comprising the steps of charging a neutralized test fabric optionally by contacting with a charging fabric; presenting the charged test fabric a predetermined distance, e.g., less than 5 inches or less than 2 inches, from a static-influenced agent (present in a pre-measured amount) such that at least a portion of the static-influenced agent attaches to the charged test fabric; and determining the quantity of attached static-influenced agent. The predetermined distance may be based on properties of the static-influenced agent. In some aspects, the charging comprises tribocharging the neutralized test fabric. In some aspects, the tribocharged test fabric has an electric potential of greater than ±0 kV. In some aspects, the tribocharging comprises rubbing the charging fabric along a surface of the neutralized test fabric at a speed from 1 in/s to 50 in/s. In some aspects, the charged test fabric has an electric potential of greater than ±0 kV. In some aspects of the method, the charging comprises tumbling. The method may further comprise the step of conditioning the neutralized test fabric and/or the charged test fabric to a controlled environment, e.g., one maintained at a temperature from 10° C. to 30° C. and/or a relative humidity from 0% to 70%, e.g., from 0% to 30%. The method may further comprise the step of neutralizing a base fabric to yield the neutralized test fabric, and this step may comprise washing and drying the test fabric and conditioning the test fabric to the controlled environment. The neutralizing may further comprise neutralizing the static charge of the test fabric and/or measuring the electric charge of the charged test fabric. The test fabric may comprise natural fibers, synthetic fibers of polyester, polyamide, polyalkene, or polyacrylic, composite fibers, woven or non-woven fabrics, laminate fabrics, or combinations of natural and synthetic fibers, or blends thereof. The charging fabric may comprise natural fibers, synthetic fibers of polyester, polyamide, polyalkene, or polyacrylic, composite fibers, woven or non-woven fabrics, laminate fabrics, or combinations of natural and synthetic fibers, or blends thereof; for example, nylon-6,6, PET, wool, wool blends, nylon-cotton blends, or combinations thereof. The static-influenced agent may comprise polyester lint, cotton lint, human hair, cat hair, dog hair, dust, pollen, allergens, irritants, spores, or combinations thereof.

BRIEF DESCRIPTION OF THE DRAWINGS

The disclosure is described in detail below with reference to the appended drawings, wherein like numerals designate similar parts.

FIG. 1 is a graph showing the charge generated on a test fabric vs. the attraction propensity for various static-influenced agents.

DETAILED DESCRIPTION

Introduction

As noted above, conventional fabrics tend to attract and collect various unwanted static-influenced particles, such as lint, hair, or dust due to electrostatic attractive force between the particles and the fabric. The collection of such particles on clothing has long been deemed a nuisance—consumers generally want their clothes to be free of such particles. Often it is the static properties of the fabric that lead to the attraction/collection of these particles. Some known test methods measure the ability of a fabric to dissipate charge. While these methods provide useful information about the static performance of a fabric, they fail to quantitatively show how a fabric will behave in the presence of static-influenced agents. These methods do not provide a quantitative method for determining a fabric's propensity for static attraction (and accumulation) of particles.

In some embodiments, the present disclosure relates to a method for accurately measuring the attraction propensity of a fabric, e.g., the propensity of a fabric to attract (and/or accumulate) static-influenced agents, such as lint, hair, dust and others. Due to the pioneering nature of the disclosure, there is minimal, if any, relevant prior art—generally, the art relates to static discharge testing or static information.

The inventors have now discovered that standardizing both the charge on a test fabric and the predetermined distance away from a static-influenced agents that the test fabric is positioned surprisingly provides for a highly quantitative and accurate measurement of a test fabric's propensity for static attraction, e.g., how much static-influenced agent it attracts. Importantly, it has been found that the disclosed method can be employed to measure the attraction propensity of a fabric that contains an antistatic agent, e.g., an antistatic fiber. This advantageously provides a metric for the effectiveness of the antistatic agent, which can be determined, e.g., by measuring (under the same standardized parameters) a similar fabric that does not contain the antistatic agent and comparing the two.

In addition, the method provides an approach for assessing the propensity of a given fabric to build up charge as well as an approach for assessing the correlation between the electric charge of a given fabric and the propensity of the fabric to attract and accumulate static-influenced agents.

The method comprises the steps of charging a neutralized test fabric and presenting the charged test fabric a predetermined distance from a static-influenced agent such that (at least a portion of) the static-influenced agent attaches to the charged test fabric. As noted above, the standardization of these parameters provides for/contributes to effectiveness of the measurement.

The method further comprises the step of determining the quantity of static-influenced agent that is attached/has attached to the test fabric. Advantageously, the quantity of static-influenced agent serves as a quantitative measurement of the fabric's attraction propensity. Generally speaking, different fabrics will inherently have different propensities to generate and dissipate charge and therefore will have different degrees of attractiveness. By determining the respective quantity of attached static-influenced agent for each, the attraction propensities can beneficially be analyzed and compared.

Preparing a Test Fabric

The test fabric (or the base fabric), generally speaking, is the fabric being measured for attraction propensity. And, in some embodiments, the test fabric is prepared from the base fabric. The standardization of the preparation, along with the charging and presentation step, will provide for/contribute to the overall effectiveness of the measurement. The test fabric (or the base fabric from which it is prepared) to be utilized in the method may vary widely.

Generally, the base fabric (and the resultant test fabric) may be formed, e.g., woven, braided, or knitted, from fibers. The features and composition of the fibers may vary widely. The base fabric is preferably formed with adequate mechanical integrity so to withstand rubbing without damage, e.g., in embodiments wherein the base fabric is tribocharged by rubbing as discussed below.

In some embodiments, the (base) fabric comprises natural fibers, synthetic fibers, composite fibers, or combinations thereof. In some cases, the synthetic fibers comprise polyester, polyamide, polyalkene, or polyacrylic fibers, or combinations thereof. In some embodiments, the test fabric comprises combinations of natural and synthetic fibers. In some embodiments, the test fabric comprises fiber blends. In some embodiments, the test fabric comprises a woven or a non-woven fabric. In some embodiments, the test fabric comprises a laminate fabric.

In some cases, the (base) fabric is neutral or capable of neutralization, e.g., the test fabric has or is capable of attaining a neutral static charge, e.g., little or no positive or negative charge. In some embodiments, the neutralized test fabric may have an electric potential less than ±5 kV, e.g., less that ±4 kV, less than ±3 kV, less than ±2 kV, less than ±1 kV, less than ±0.5 kV, or less than ±0.1 kV. In one embodiment, the neutralized test fabric has an electric potential of approximately 0 kV.

In order to ensure accuracy and precision of measurement, some embodiments of the method disclosed herein include a step of neutralizing the base fabric to yield the neutralized test fabric. In some embodiments, the fabric is neutralized prior to presentation and measurement. The base fabric may be neutralized by any method known in the art. In one embodiment, for example, the base fabric may be neutralized by an ionizing anti-static gun. One example of a commercially available anti-static gun that may be used in neutralizing the test fabric is the Cleanroom Ionizing Blow-Off Gun by Terra Universal. In one embodiment, for another example, the base fabric may be neutralized by an ionizing bar static eliminator. One example of a commercially available ionizing bar static eliminator is the Staticmaster 2U500 Ionizing Cartridge by NRD.

The test fabric is preferably clean and dry. In some embodiments, the test fabric may be cleaned, e.g., washed, and dried prior to measurement. In these embodiments, the test fabric may be cleaned, e.g., washed, and dried by any method known in the art. In embodiments wherein the test fabric is cleaned, the method of cleaning should be suitably consistent so as to ensure precision and accuracy. One example of a suitable method for cleaning the test fabric is described in AATCC M6-2016, which is incorporated herein in its entirety.

Charging Test Fabric

As noted above, the accumulation of static-influenced agents on a fabric surface is generally the result of electrostatic forces and attraction between opposite charges on the fabric surface and the static-influenced agents. Thus, a test fabric must be electrostatically charged in order to measure the attraction propensity of the fabric. Furthermore, in order to ensure the accuracy and reproducibility of such measurements, the method of charging the test fabric must be sufficiently precise.

According to the method disclosed herein, the test fabric is charged. Generally, any known technique for charging fabric may be used to charge the test fabric in the present method, so long as the technique is sufficiently precise to ensure the accuracy and reproducibility of the measurement. In some embodiments, the test fabric is charged by contacting the test fabric with a charging fabric.

In some cases, the charging is achieved by contacting the test fabric with a charging fabric. The contact with the test fabric allows for the transfer of electrons between the test fabric and the charging fabric.

One exemplary technique for charging the test fabric for the method disclosed herein is triboelectric charging (also known as tribocharging). Tribocharging refers to a type of contact electrification, whereby a first material, e.g., the neutralized test fabric, becomes electrically charged after the first material separates from another material, e.g., a charging fabric, with which it was in contact. Various factors can be manipulated to affect the strength of the charge developed by tribocharging. Rubbing the materials, e.g., the neutralized test fabric and the charging fabric, together may lead to the static charge that builds on either material. In some embodiments, the neutralized test fabric is charged by tribocharging by contacting, e.g., rubbing, the charging fabric on the test fabric. The inventors have found that tribocharging advantageously provides for superior charge buildup. Beneficially, this superior charge buildup allows for excellent attachment and/or accumulation of static-influenced agent, which provides for better overall accuracy of the measurement. Furthermore, the inventors have found that tribocharging allows for more consistent charge generation. In particular, the inventors have found that tribocharging according to the embodiments disclosed herein allows for the consistent generation of static charge on the test fabric.

In some cases, certain imprecisions of the charging process are mitigated by employing certain process parameters. This is especially true for tribocharging. In particular, it has been discovered that, by ensuring that certain parameters, e.g., length of the surface rubbed, number of times the surface is rubbed, speed of rubbing, pressure of rubbing, length of time, are controlled, tribocharging is a particularly effective technique for charging the test fabric. As noted below, the temperature and humidity of the test environment also affect the generation of charge.

As noted above, in some embodiments, tribocharging comprises contacting, e.g., rubbing a charging fabric on the test fabric to yield the charged test fabric. When charging by tribocharging, the charging fabric is typically rubbed along at least a portion of the surface of the test fabric. In some embodiments, the charging fabric is rubbed along the surface of the test fabric by hand, e.g., by a user holding the charging fabric and rubbing it along the surface of the test fabric. In some embodiments, the charging fabric may be affixed or otherwise secured to another object to facilitate rubbing the charging fabric along the surface of the test fabric by hand. For example, the charging fabric may be affixed to a wooden block, which may be easier to handle. In other embodiment, the charging fabric may be rubbed along the surface of the test fabric by a robotic or mechanical device.

When charging the test fabric by tribocharging by rubbing, the charging fabric is typically rubbed along a length of the surface of the test fabric. In some embodiments, the charging fabric is rubbed along a specific length of the surface of the test fabric. In one embodiment, for example, the charging fabric is rubbed along the entire length of the surface of the test fabric, e.g., 100% of the length. In some embodiments, the charging fabric is rubbed along less than entire length of the surface of the test fabric, e.g., greater than 90% of the length, greater than 80% of the length, greater than 70% of the length, greater than 60% of the length, greater than 50% of the length, or greater than 40% of the length.

In some embodiments, the charging fabric may be rubbed along a length of the test fabric a specific number of times. In one embodiment, for example, the test fabric is rubbed along a length of the test fabric only once. In some embodiments, the test fabric is rubbed along a length of the fabric multiple times, e.g., at least one time, at least two times, at least three times, at least four times, at least five times, at least six times, or at least seven times.

As noted, in embodiments wherein the test fabric is tribocharged by rubbing, the charging fabric may be rubbed along a specific length of the test fabric and may be rubbed along the length of the test fabric multiple times. In some embodiments, the charging fabric is rubbed along the surface of the test fabric multiple times and rubs along approximately the same specified length of the surface each time. For example, in one embodiment, the test fabric is charged by rubbing the charging fabric along at least 90% of the surface of the test fabric at least 5 times. In some embodiments, the charging fabric may be rubbed along varying specified lengths of the test fabric each time. For example, in one embodiment, the test fabric is charged by rubbing the charging fabric along the test fabric five times and each time alternates between rubbing along at least 50% of the surface of the test fabric and along at least 80% of the surface of the test fabric.

In some embodiments, the charging fabric may be rubbed along the surface of the test fabric at a specific speed. In one embodiment, the charging fabric is rubbed along the surface of the test fabric at a speed from 1 in/s to 50 in/s, e.g., from 1 in/s to 45 in/s, from 1 in/s to 40 in/s, from 1 in/s to 35 in/s, from 1 in/s to 30 in/s, from 1 in/s to 25 in/s, from 2 in/s to 50 in/s, from 2 in/s to 45 in/s, from 2 in/s to 40 in/s, from 2 in/s to 35 in/s, from 2 in/s to 30 in/s, from 2 in/s to 25 in/s, from 3 in/s to 50 in/s, from 3 in/s to 45 in/s, from 3 in/s to 40 in/s, from 3 in/s to 35 in/s, from 3 in/s to 30 in/s, from 3 in/s to 25 in/s, from 5 in/s to 50 in/s, from 5 in/s to 45 in/s, from 5 in/s to 40 in/s, from 5 in/s to 35 in/s, from 5 in/s to 30 in/s, from 5 in/s to 25 in/s, from 8 in/s to 50 in/s, from 8 in/s to 45 in/s, from 8 in/s to 40 in/s, from 8 in/s to 35 in/s, from 8 in/s to 30 in/s, or from 8 in/s to 25 in/s. In terms of lower limits, the charging fabric may be rubbed along the surface of the test fabric at a speed greater than 1 in/s, e.g., greater than 2 in/s, greater than 3 in/s, greater than 5 in/s, or greater than 8 in/s. In terms of upper limits, the charging fabric may be rubbed along the surface of the test fabric at a speed less than 50 in/s, e.g., less than 45 in/s, less than 40 in/s, less than 35 in/s, less than 30 in/s, or less than 25 in/s.

In some embodiments, the tribocharging is preferably accomplished relatively quickly. As noted above, fabrics may inherently have different propensities to dissipate static charge. As a result, some test fabrics may dissipate the charge generated by tribocharging and the charge developed by tribocharging may quickly decay. It is therefore desirable that the tribocharging be performed quickly, e.g., to reduce variability in testing due to charge dissipation. In one embodiment, for example, tribocharging the test fabric is completed in less than five minutes, e.g., less than four minutes, less than three minutes, less than two minutes, less than one minute, or less than 30 seconds.

In some embodiments, the charging fabric is preferably rubbed along the surface of the test fabric at approximately constant pressure. Pressure will affect the frictional force between the charging fabric and the test fabric. As a result, pressure affects the exchange of electrons between the charging fabric and the test fabric. Variation in pressure may allow for undesirable inconsistency in charge generation. It is therefore desirable that constant pressure be applied.

In one embodiment, the charging fabric is rubbed along the surface of the test fabric at an approximately constant pressure of from 50 to 250 Pa, e.g., from 50 to 225 Pa, from 50 to 200 Pa, from 50 to 175 Pa, from 50 to 150 Pa, from 55 to 250 Pa, from 55 to 225 Pa, from 55 to 200 Pa, from 55 to 175 Pa, from 55 to 150 Pa, from 60 to 250 Pa, from 60 to 225 Pa, from 60 to 200 Pa, from 60 to 175 Pa, from 60 to 150 Pa, from 65 to 250 Pa, from 65 to 225 Pa, from 65 to 200 Pa, from 65 to 175 Pa, from 65 to 150 Pa, from 70 to 250 Pa, from 70 to 225 Pa, from 70 to 200 Pa, from 70 to 175 Pa, or from 70 to 150 Pa. In terms of lower limits, the charging fabric may be rubbed at an approximately constant pressure greater than 50 Pa, e.g., greater than 55 Pa, greater than 60 Pa, greater than 65 Pa, or greater than 70 Pa. In terms of upper limits, the charging fabric may be rubbed at an approximately constant pressure less than 250 Pa, e.g., less than 225 Pa, less than 200 Pa, less than 175 Pa, or less than 150 Pa.

Maintaining approximately constant pressure may be facilitated by the use of a block or mechanically-controlled rubbing, as described above. In some embodiments, for example, a block of a specific mass can be used to ensure approximately constant pressure. In one embodiment wherein a block is used, the block has a mass of less than 250 g, e.g., less than 200 g, less than 150 g, less than 125 g, less than 100 g, or less than 75 g. In terms of lower limits, the block may have a mass greater than 25 g, e.g., greater than 30 g, greater than 35 g, greater than 40 g, greater than 45 g, or greater than 50 g. In terms of ranges, the block may have a mass from 25 g to 250 g, e.g., from 25 g to 200 g, from 25 g to 150 g, from 25 g to 125 g, from 25 g to 100 g, from 25 g to 75 g, from 30 g to 250 g, from 30 g to 200 g, from 30 g to 150 g, from 30 g to 125 g, from 30 g to 100 g, from 30 g to 75 g, from 35 g to 250 g, from 35 g to 200 g, from 35 g to 150 g, from 35 g to 125 g, from 35 g to 100 g, from 35 g to 75 g, from 40 g to 250 g, from 40 g to 200 g, from 40 g to 150 g, from 40 g to 125 g, from 40 g to 100 g, from 40 g to 75 g, from 45 g to 250 g, from 45 g to 200 g, from 45 g to 150 g, from 45 g to 125 g, from 45 g to 100 g, from 45 g to 75 g, from 50 g to 250 g, from 50 g to 200 g, from 50 g to 150 g, from 50 g to 125 g, from 50 g to 100 g, or from 50 g to 75 g.

In some embodiments, the tribocharging of the test fabric is achieved by tumbling, e.g., in a tumble dryer. In some embodiments, the neutralized test fabric is tribocharged by contacting the charging fabric on the test fabric while tumbling, e.g., in a tumble dryer. One example of a commercially available tumble dry that may be used to tribocharge by tumbling is Kenmore Series 6005. In these embodiments, the neutralized test fabric and/or the charging fabric may be placed in a tumble dryer and tumbled at an elevated temperature for sufficient time to allow adequate buildup of electrostatic charge. In some embodiments, the neutralized test fabric and/or the charging fabric are tumbled for at least 5 minutes, e.g., at least 8 minutes, at least 10 minutes, at least 12 minutes, or at least 15 minutes. In some embodiments, the neutralized test fabric and/or the charging fabric are tumbled at a temperature greater than 40° C., e.g., greater than 45° C., greater than 50° C., greater than 55° C., or greater than 60° C.

While the technique for charging the test fabric is not particularly limited, the test fabric preferably develops some amount of electrostatic charge to yield the charged test fabric. Said another way, the charged test fabric preferably has a non-zero electric potential. In one embodiment, the charged test fabric has an electric potential greater than ±0 kV, e.g., greater than ±0.1 kV, greater than ±0.2 kV, greater than ±0.5 kV, greater than ±0.7 kV, or greater than ±1 kV.

The charging fabric, which is used to charge the test fabric, is not particularly limited. The charging fabric may have the same composition of the test fabric, or the charging fabric may have a different composition from the test fabric. Generally, the charging fabric is formed, e.g., woven, braided, or knitted, from fibers. In some embodiments, the charging fabric comprises natural fibers, synthetic fibers of polyester, polyamide, polyalkene, or polyacrylic, or composite fibers. In some embodiments, the charging fabric comprises combinations of natural and synthetic fibers. In some embodiments, the charging fabric comprises fiber blends. In some embodiments, the charging fabric comprises fibers of nylon-6,6, PET, wool, wool blends, nylon-cotton blends, or combinations thereof. In some embodiments, the charging fabric comprises a woven or a non-woven fabric. In some embodiments, the test fabric comprises a laminate fabric.

In some embodiments, the charging fabric is neutralized prior to tribocharging. The charging fabric may be neutralized by any method suitable for the neutralization of the base fabric, as discussed above. In some embodiments, both the base fabric and the charging fabric are neutralized by the same method.

The tribocharging and/or other method which imparts a charge on the test fabric may also impart a charge on the charging fabric. In some embodiments, the charging fabric develops some amount of electrostatic charge. Said another way, the charging fabric may have a non-zero electric potential. In one embodiment, the charging fabric has an electric potential greater than ±0 kV, e.g., greater than ±0.1 kV, greater than ±0.2 kV, greater than ±0.5 kV, greater than ±0.7 kV, or greater than ±1 kV.

In some embodiments, the test fabric is tribocharged with the charging fabric to yield the charged test fabric, and both the charging fabric and the charged test fabric develop a non-zero electric potential. In some embodiments, the charging fabric may develop an electric potential that is approximately equal to that developed on the charged test fabric. In other of these embodiments, the charging fabric may develop an electric potential that is greater or less than that of the charged test fabric. In these embodiments, the charging fabrics typically develops a charge of opposite polarity relative to the test fabric.

As noted above, different types of fabrics may respond to controlled environment differently, e.g., behave differently in the controlled environment, and allowing fabric to adequately equilibrate to the controlled environment is desirable to ensure success, repeatability, and/or reproducibility of the method disclosed herein. In some embodiments, the charged test fabric may be conditioned to the controlled environment. For example, the charged test fabric may be exposed to the controlled environment for at least 1 hour, e.g., at least 2 hours, at least 6 hours, at least 12 hours, at least 24 hours, or at least 36 hours.

Controlled Environment

The present inventors have found that the disclosed method and the individual steps thereof are particularly affected by the environment in which the method is performed. For example, the present inventors have found that certain environmental conditions, such as temperature, pressure, and relative humidity, may have an impact on the success, repeatability, and/or reproducibility of the method. The present inventors believe that these and other environmental conditions affect the generation of electrostatic charge. In particular, the inventors believe that these environmental conditions affect the generation and dissipation of electrostatic charge by tribocharging. Therefore, the method and/or the individual steps thereof is preferably carried out in a controlled environment, e.g., a controlled temperature and humidity room (known as a "CTH room"). In some embodiments, all the individual steps of the method are carried out in a CTH room.

The controlled environments, e.g., those discussed herein, are applicable to one or more of the individual steps as well as to the method as a whole.

In some embodiments, the controlled environment includes controlled temperature. In one embodiment, the controlled environment is maintained at a temperature from 10° C. to 30° C., e.g., from 10° C. to 29° C., from 10° C. to 28° C., from 10° C. to 27° C., from 10° C. to 26° C., from 10° C. to 25° C., from 12° C. to 30° C., from 12° C. to 29° C., from 12° C. to 28° C., from 12° C. to 27° C., from 12° C. to 26° C., from 12° C. to 25° C., from 15° C. to 30° C., from 15° C. to 29° C., from 15° C. to 28° C., from 15° C. to 27° C., from 15° C. to 26° C., from 15° C. to 25° C., from 17° C. to 30° C., from 17° C. to 29° C., from 17° C. to 28° C., from 17° C. to 27° C., from 17° C. to 26° C., from 17° C. to 25° C., from 20° C. to 30° C., from 20° C. to 29° C., from 20° C. to 28° C., from 20° C. to 27° C., from 20° C. to 26° C., or from 20° C. to 25° C. In terms of lower limits, the controlled environment may be maintained at a temperature greater than 10° C., e.g., greater than 12° C., greater than 15° C., greater than 17° C., or greater than 20° C. In terms of upper limits, the controlled environment may be maintained at a temperature less than 30° C., e.g., less than 29° C., less than 28° C., less than 27° C., less than 26° C., or less than 25° C.

In some embodiments, the controlled environment includes controlled relative humidity. In one embodiment, the controlled environment is maintained at a relative humidity from 0% to 70%, e.g., from 0% to 60%, from 0% to 50%, from 0% to 40%, from 0% to 30%, from 0% to 20%, from 1% to 70%, from 1% to 60%, from 1% to 50%, from 1% to 40%, from 1% to 30%, from 1% to 20%, from 2% to 70%, from 2% to 60%, from 2% to 50%, from 2% to 40%, from 2% to 30%, from 2% to 20%, from 5% to 70%, from 5% to 60%, from 5% to 50%, from 5% to 40%, from 5% to 30%, from 5% to 20%, from 7% to 70%, from 7% to 60%, from 7% to 50%, from 7% to 40%, from 7% to 30%, from 7% to 20%, from 10% to 70%, from 10% to 60%, from 10% to 50%, from 10% to 40%, from 10% to 30%, or from 10% to 20%. In terms of lower limits, the controlled environment may be maintained at a relative humidity greater than 0%, e.g., greater than 1%, greater than 2%, greater than 5%, greater than 7%, or greater than 10%. In terms of upper limits, the controlled environment may be maintained at a relative humidity less than 70%, e.g., less than 60%, less than 50%, less than 40%, less than 30%, or less than 20%.

Different types of fabrics may respond to controlled environment differently, e.g., behave differently in the controlled environment. For example, fibers of different compositions may have differing propensities to absorb water when exposed to a humid environment, such as the controlled environment. In order to ensure success, repeatability, and/or reproducibility, it is therefore desirable that fabric be allowed to adequately equilibrate to the controlled environment.

In some embodiments, the test fabric, e.g., the neutralized test fabric, may be conditioned to the controlled environment. For example, the test fabric may be exposed to the controlled environment for at least 1 hour, e.g., at least 2 hours, at least 6 hours, at least 12 hours, at least 24 hours, or at least 36 hours.

Presentation of the Charged Test Fabric/Determination of Quantity

In order to assess the propensity of the charged fabric to attract and accumulate static-influenced agents, the charged test fabric is presented to a static-influenced agent. In particular, according to embodiments the method disclosed herein, the charged test fabric is presented at a predetermined distance from a static-influenced agent, such that at least a portion of the static-influenced agent attaches to the charged test fabric. By determining the quantity of static-influenced agent attached to the charged test fabric, the attraction propensity, can be assessed.

In some embodiments, the static-influenced agent is configured in a pre-measured amount or quantity. For example, the static-influenced agent may be configured as a pile (or other shape) of a certain mass. In one embodiment, for example, the static-influenced agent may be a pre-measured pile (or other shape) of from 0.01 mg to 20 mg of static-influenced agent, e.g., from 0.01 mg to 15 mg, from 0.01 mg to 10 mg, from 0.01 mg to 5 mg, from 0.01 mg to 1 mg, from 0.05 mg to 20 mg, from 0.05 mg to 15 mg, from 0.05 mg to 10 mg, from 0.05 mg to 5 mg, from 0.05 mg to 1 mg, from 0.1 mg to 20 mg, from 0.1 mg to 15 mg, from 0.1 mg to 10 mg, from 0.1 mg to 5 mg, from 0.1 mg to 1 mg, from 0.15 mg to 20 mg, from 0.15 mg to 15 mg, from 0.15 mg to 10 mg, from 0.15 mg to 5 mg, from 0.15 mg to 1 mg, from 0.2 mg to 20 mg, from 0.2 mg to 15 mg, from 0.2 mg to 10 mg, from 0.2 mg to 5 mg, from 0.2 mg to 1 mg, from 0.25 mg to 20 mg, from 0.25 mg to 15 mg, from 0.25 mg to 10 mg, from 0.25 mg to 5 mg, or from 0.25 mg to 1 mg. In terms of lower limits, the static-influenced agent may be a pre-measured pile (or other shape) of greater than 0.01 mg (10 micrograms), e.g., greater than 0.05 mg, greater than 0.1 mg, greater than 0.15 mg, greater than 0.2 mg, or greater than 0.25 mg. In terms of upper limits, the static-influenced agent may be a pre-measured pile (or other shape) of less than 20 mg, e.g., less than 15 mg, less than 10 mg, less than 5 mg, or less than 1 mg.

In some embodiments, the charged test fabric is presented to multiple pre-measured piles (or other shapes) of static-influenced agent. For example, the charged test fabric may be presented to at least two piles (or other shapes), e.g., at least three, at least four, at least five, or at least six. Presenting the charged test fabric to multiple pre-measured piles may be particularly desirable, because it may provide for a more quantitative metric of the attractiveness of the charged fabric. That is, the propensity of the charged fabric to attract static-influenced agents can be assessed by counting the number of pre-measured piles (or other shapes) of static-influenced agents that attach to the charged test fabric. For example, a particular charged fabric may "pick up" three of a possible five pre-measured piles. In some cases, the number of piles is used as the attraction propensity metric (see discussion below).

The inventors have found that it is critical to present the charged test fabric to the static-influenced agent at a predetermined distance. Use of a predetermined distance provides for consistency of the measurement from sample-to-sample. Although the predetermined distance is not particularly limited and may vary widely, the strength of electrostatic forces between the charged tests fabric and the static-influenced agent reduces with distance. Specifically, the attractive force is inversely proportional to the square of the distance of separation. Thus, the method will be ineffective if the predetermined distance is too great.

In some embodiments, the predetermined distance may be based on properties of the static-influenced agent. For example, the present inventors have found that some static-influenced agents are especially susceptible to polarization. As a result, the predetermined distance may be greater for those static-influenced agents.

In one embodiment, the predetermined distance is less than 5 inches, e.g., less than 3 inches, less than 2 inches, less than 1.75 inches, less than 1.5 inches, or less than 1.25 inches. In terms of lower limits, the predetermined distance may be greater than 0 inches, e.g., greater than 0.25 inches, greater than 0.5 inches, or greater than 0.75 inches. In terms of ranges, the predetermined distance may be from 0 inches to 5 inches, e.g., from 0 inches to 3 inches, from 0 inches to 2 inches, from 0 inches to 1.75 inches, from 0 inches to 1.5 inches, from 0 inches to 1.25 inches, from 0.25 inches to 5 inches, from 0.25 inches to 3 inches, from 0.25 inches to 2 inches, from 0.25 inches to 1.75 inches, from 0.25 inches to 1.5 inches, from 0.25 inches to 1.25 inches, from 0.5 inches to 5 inches, from 0.5 inches to 3 inches, from 0.5 inches to 2 inches, from 0.5 inches to 1.75 inches, from 0.5 inches to 1.5 inches, from 0.5 inches to 1.25 inches, from 0.75 inches to 5 inches, from 0.75 inches to 3 inches, from 0.75 inches to 2 inches, from 0.75 inches to 1.75 inches, from 0.75 inches to 1.5 inches, or from 0.75 inches to 1.25 inches.

The degree to which the static-influenced agents may be polarized and thereby attracted to the test fabric may also be affected by an electrostatic charge on the static-influenced agents. For example, a static-influenced agent may develop a non-zero electric potential prior to presentation of the charged test fabric. Such a non-zero electric potential may alter attraction propensity. Thus, in some embodiments, the static-influenced agents may by neutralized prior to presentation of the charged test fabric.

As noted above, many types of static-influenced agents may be employed to attach to or accumulate on fabric. The composition of the static-influenced agent used in the method described herein is not particularly limited, and any suitable static-influenced agent (or combinations of agents) may be used. In some embodiments, the static-influenced agent may comprise lint, such as polyester lint or cotton lint, hair, such as human hair or pet hair, e.g., dog hair or cat hair, dust pollen, allergens, irritants, spores or combinations thereof. In some embodiments, the static-influenced agent may be a combination meant to simulate lint found in typical household dryers. For example, the static-influenced agent may be a combination of polyester lint, cotton lint, and hair.

The quantity of static-influenced agent attached to the charged test fabric can be determined by any method known in the art. In some embodiments, the quantity of attached static-influenced agent can be determined by visual observation. For example, in embodiments where the charged test fabric is presented to multiple pre-measured piles (or other shapes) of static-influenced agents, the quantity of static-influenced agent attached can be determined by counting the number of pre-measured piles attached to the surface of the charged test fabric or, conversely, the number of pre-measured piles that remain unattached. In such cases, the number of counted piles is used as the attraction propensity metric.

In some embodiments, the total mass or total weight of the attached static-influenced agent may be measured and used as the attraction propensity metric. In some embodiments, the mass or weight of attached static-influenced agent can be determined by determining the difference in weight or mass of the charged test fabric, e.g., measurement of the combined fabric and static-influenced agent and subtracting the known initial mass of the fabric.

In some embodiments, the total mass or total weight to the unattached static-influenced agent may be measured and used as the attraction propensity metric.

Additional Steps

Some embodiments of the disclosed method may include additional steps.

In some embodiments, the electric charge (also known as charge buildup) of the charged test fabric may be measured. As noted above, while the nature of electrostatic forces and attraction between fabric and static-influenced agents is understood, the correlation between static charge and attractiveness can be reduced to a quantitative relationship. By measuring the electric charge of the test fabric concurrently with measuring the attractiveness of the fabric, data can be collected that may be used to quantify that correlation.

Various methods of measuring electric charge are known in the art, and any such method may be utilized herein. In some embodiments, the electric charge of the charged test fabric may be measured by a non-contact electrometer. One example of a commercially available non-contact electrometer that may be used in measuring the electric charge of the charged test fabric is the SK-H050 Electrostatic Sensor by Keyence.

As noted above, the fabric, e.g., the base fabric or the test fabric, may be prepared for analysis by the present method by various steps, such as washing, drying, and neutralizing. In some embodiments, the fabric may undergo further preparation. For example, the base fabric may be cut and/or otherwise shaped into an appropriate testing size.

In some embodiments, the base fabric is cut to a specific shape, for example, a square, a rectangle, a circle, or a triangle. In some embodiments, the base fabric is cut to a specific surface area. In one embodiment, the base fabric is cut to a surface area from 1 $in^2$ to 100 $in^2$, e.g., 1 $in^2$ to 90 $in^2$, 1 $in^2$ to 80 $in^2$, 1 $in^2$ to 70 $in^2$, 1 $in^2$ to 60 $in^2$, 1 $in^2$ to 50 $in^2$, from 2 $in^2$ to 100 $in^2$, 2 $in^2$ to 90 $in^2$, 2 $in^2$ to 80 $in^2$, 2 $in^2$ to 70 $in^2$, 2 $in^2$ to 60 $in^2$, 2 $in^2$ to 50 $in^2$, from 5 $in^2$ to 100 $in^2$, 5 $in^2$ to 90 $in^2$, 5 $in^2$ to 80 $in^2$, 5 $in^2$ to 70 $in^2$, 5 $in^2$ to 60 $in^2$, 5 $in^2$ to 50 $in^2$, from 10 $in^2$ to 100 $in^2$, 10 $in^2$ to 90 $in^2$, 10 $in^2$ to 80 $in^2$, 10 $in^2$ to 70 $in^2$, 10 $in^2$ to 60 $in^2$, 10 $in^2$ to 50 $in^2$, from 15 $in^2$ to 100 $in^2$, 15 $in^2$ to 90 $in^2$, 15 $in^2$ to 80 $in^2$, 15 $in^2$ to 70 $in^2$, 15 $in^2$ to 60 $in^2$, 15 $in^2$ to 50 $in^2$, from 20 $in^2$ to 100 $in^2$, 20 $in^2$ to 90 $in^2$, 20 $in^2$ to 80 $in^2$, 20 $in^2$ to 70 $in^2$, 20 $in^2$ to 60 $in^2$, or 20 $in^2$ to 50 $in^2$. In terms of lower limits, the base fabric may be cut to a surface area greater than 1 $in^2$, e.g., greater than 2 $in^2$, greater than 5 $in^2$, greater than 10 $in^2$, greater than 15 $in^2$, or greater than 20 $in^2$. In terms of upper limits, the base fabric may be cut to a surface area less than 100 $in^2$, e.g., less than 90 in $in^2$, less than 80 $in^2$, less than 70 $in^2$, less than 60 $in^2$, or less than 50 $in^2$.

Examples

The present disclosure will be further understood by reference to the following non-limiting examples.

Example 1

The disclosed method was used to measure the attraction propensity of four samples of polyester fabrics. More specifically, the method was used to quantify the effectiveness of the anti-static yarn as a component of the fabric. Samples 1 and 2 were fleece fabrics made of polyester. Sample 2 had quantities of anti-static yarn as a component of the fabric; Sample 1 did not. Samples 3 and 4 are woven fabrics made of polyester. Sample 4 had quantities of anti-static yarn as a component of the fabric; Sample 3 did not.

The test samples were tribocharged by rubbing with a charging fabric. The charging fabric comprised 100% melt spun nylon-6,6 woven fabric. The charging fabric was rubbed along the entire length of the surface of each sample at least ten times at an approximately constant pressure of about 85 Pa. The electric charge of each sample was measured prior to presenting the charged test fabrics to the static-influenced agent (see "Charge" column). Each sample was presented to four sets of static-influenced agents: polyester lint, cotton lint, cat hair, and dog hair, at a consistent, predetermined distance of 1 inch. Each set comprised four piles of the respective agent. Each sample was charged and presented to the four sets of four piles three times. Average results of the three tests on each sample are reported in Table 1 below:

TABLE 1

| | | Static-Influenced Agent Attached (%) | | | |
|---|---|---|---|---|---|
| Sample | Charge (kV) | Polyester Lint | Cotton Lint | Cat Hair | Dog Hair |
| 1 | −12.3 | 100 | 83 | 100 | 100 |
| 2 | −1.8 | 0 | 0 | 33 | 58 |
| 3 | −18.0 | 83 | 100 | 50 | 58 |
| 4 | −1.6 | 0 | 0 | 0 | 0 |

Differentiations in static attraction propensity for various fabrics were effectively demonstrated by utilizing the disclosed testing methods. These differentiations can be used to evaluate the performance of the fabrics.

For example, using the disclosed testing method, it was quantitatively determined that Sample 2 demonstrates a much lower attraction propensity than Sample 1 (0 vs. 100; 0 vs. 83; 33 vs. 100; and 58 vs. 100, respectively). Similarly, Sample 4 demonstrates a much lower attraction propensity than Sample 3. Thus, the disclosed method can be used to quantitatively demonstrate the anti-static benefits achieved by the anti-static yarn. Sample 2 and Sample 4, with their anti-static yarn component, provide for a significant reduction in attraction propensity.

Furthermore, using the disclosed testing method, the quantitative relationship between the charge generated on a specific fabric and the attraction propensity of that fabric can be determined. As the results of Table 1 illustrate, Samples 1 and 3 developed much greater charges than Samples 2 and 4. As a result of the greater charges, Samples 1 and 3 demonstrate a much higher attraction propensity. Thus, the disclosed test method can be utilized to compare the propensities to attract lint of various fabrics, which is a reflection of the anti-static properties of the various fabrics resulting from, e.g., fabric construction and composition.

FIG. 1 shows attraction propensities generated for various static-influenced agents. As shown, polyester lint, cotton lint, cat hair, and dog hair all demonstrate the ability to effectively measure attraction propensity of a given fabric. In some cases, polyester lint seems to be particularly effective.

Example 2

The disclosed method was used to determine the loading of anti-static fibers needed for a desired level of product functionality. More specifically, the method was used to quantify the effectiveness of varying amounts of an anti-static yarn as a component of the fabric. Five samples were prepared as woven polyester fabrics. Each sample contained a varying amount of an anti-static yarn, as indicated in Table 2.

The test samples were tribocharged by rubbing with a charging fabric. The charging fabric comprised 100% melt spun nylon-6,6 woven fabric. The charging fabric was rubbed along the entire length of the surface of each sample at least ten times at an approximately constant pressure of about 85 Pa. The electric charge of each sample was measured prior to presenting the charged test fabrics to the static-influenced agent (see "Charge" column of Table 2). Each sample was presented to four sets of static-influenced agents: polyester lint, cotton lint, cat hair, and dog hair, at a consistent, predetermined distance of 1 inch. Each set comprised four piles of the respective agent. Each sample was charged and presented to the four sets of four piles three times. Average results of the three tests on each sample are reported in Table 2 below:

TABLE 2

| | | | Static-Influenced Agent Attached (%) | | | |
|---|---|---|---|---|---|---|
| Sample | Anti-Stat. Yarn | Charge (kV) | Polyester Lint | Cotton Lint | Cat Hair | Dog Hair |
| 1 | 0% | −18.0 | 83 | 100 | 50 | 58 |
| 2 | 0.2% | −2.1 | 42 | 50 | 50 | 50 |
| 3 | 0.4% | −2.1 | 67 | 75 | 42 | 42 |
| 4 | 0.8% | −1.8 | 0 | 0 | 33 | 0 |
| 5 | 1.4% | −1.6 | 0 | 0 | 0 | 0 |

Differentiations in static attraction propensity for various fabrics were effectively demonstrated by utilizing the disclosed testing methods. These differentiations can be used to determine the amount of anti-static yarn necessary to achieve certain performance characteristics.

For example, using the disclosed testing method, it was quantitatively determined that Sample 4, which includes 0.8% of an anti-static yarn, demonstrates a much lower attraction propensity for polyester lint, cotton lint, and dog hair than Sample 1 (0 vs. 83; 0 vs. 100; and 0 vs. 58, respectively). Thus, the disclosed method demonstrates that up to 0.8% of the anti-static yarn may be necessary to reduce or eliminate the attraction propensity of the fabric for polyester lint, cotton lint, and dog hair. Furthermore, the testing method quantitatively determined that Sample 5, which includes 1.4% of the anti-static yarn, demonstrates a much lower attraction propensity for cat hair than Sample 4 (0 vs. 33). Thus, the disclosed method demonstrates that up to 1.4% of the anti-static yarn may be necessary to reduce or eliminate the attraction propensity of the fabric for cat hair.

In this way, the disclosed method may be utilized to quantitatively determine the amount of anti-static fiber necessary to achieve specific performance characteristics.

Example 3

The disclosed method was again used to determine the loading of anti-static fibers needed for a desired level of product functionality. More specifically, the method was used to quantify the effectiveness of varying amounts of an anti-static yarn as a component of the fabric. Three samples were prepared as fleece polyester fabrics. Each sample contained a varying amount of an anti-static yarn, as indicated in Table 3.

The test samples were tribocharged by rubbing with a charging fabric. The charging fabric comprised 100% melt spun nylon-6,6 woven fabric. The charging fabric was rubbed along the entire length of the surface of each sample at least ten times at an approximately constant pressure of about 85 Pa. The electric charge of each sample was measured prior to presenting the charged test fabrics to the static-influenced agent (see "Charge" column of Table 3). Each sample was presented to four sets of static-influenced agents: polyester lint, cotton lint, cat hair, and dog hair, at a consistent, predetermined distance of 1 inch. Each set comprised four piles of the respective agent. Each sample was charged and presented to the four sets of four piles three times. Average results of the three tests on each sample are reported in Table 3 below:

TABLE 3

| Sample | Anti-Stat. Yarn | Fabric Charge (kV) | Static-Influenced Agent Attached (%) | | | |
|---|---|---|---|---|---|---|
| | | | Polyester Lint | Cotton Lint | Cat Hair | Dog Hair |
| 1 | 0% | −15.9 | 75 | 33 | 83 | 83 |
| 2 | 0.6% | −2.2 | 0 | 0 | 33 | 8 |
| 3 | 1% | −0.9 | 0 | 0 | 0 | 0 |

Differentiations in static attraction propensity for various fabrics were effectively demonstrated by utilizing the disclosed testing methods. These differentiations can be used to determine the amount of anti-static yarn necessary to achieve certain performance characteristics.

For example, using the disclosed testing method, it was quantitatively determined that Sample 2, which includes 0.6% of an anti-static yarn, demonstrates a much lower attraction propensity for polyester lint and cotton lint (0 vs. 75; and 0 vs. 33, respectively). Thus, the disclosed method demonstrates that up to 0.6% of the anti-static yarn may be necessary to reduce or eliminate the attraction propensity of the fabric for polyester lint and cotton lint. Furthermore, the testing method quantitatively determined that Sample 3, which includes 1% of the anti-static yarn, demonstrates a much lower attraction propensity for dog hair and cat hair than Sample 2 (0 vs. 33; and 0 vs. 8, respectively). Thus, the disclosed method demonstrates that up to 1% of the anti-static yarn may be necessary to reduce or eliminate the attraction propensity of the fabric for dog hair and cat hair.

In this way, the disclosed method may be utilized to quantitatively determine the amount of anti-static fiber necessary to achieve specific performance characteristics.

Example 4

The disclosed method was used to determine the long-term effectiveness of anti-static fibers. More specifically, the method was used to quantify the effectiveness of an anti-static yarn as a component of the fabric after washing. Three samples were prepared as woven polyester fabrics. Each sample contained a varying amount of an anti-static yarn, as indicated in Table 4. Sample 1 contained no anti-static yarn but utilized an anti-static fabric processing aid, which was applied to the surface of the fabric sample.

The test samples were tribocharged by rubbing with a charging fabric. The charging fabric comprised 100% spun nylon-6,6 woven fabric. The charging fabric was rubbed along the entire length of the surface of each sample at least ten times at an approximately constant pressure of about 85 Pa. The electric charge of each sample was measured prior to presenting the charged test fabrics to the static-influenced agent (see "Charge" column of Table 4). Each sample was presented to four sets of static-influenced agents: polyester lint, cotton lint, cat hair, and dog hair, at a consistent, predetermined distance of 1 inch. Each set comprised four piles of the respective agent. Each sample was charged and presented to the four sets of four piles three times. Average results of the three tests on each sample are reported in Table 4 below (in the rows indicated "Unw.").

After the initial tests, the three test samples were washed three times according to ATCC M6-2016 with warm water and normal agitation. The washed samples were dried, conditioned, and tribocharged in the same way. The electric charge of each was measured, and each sample was presented to four sets of static-influenced agents, as before. Charging and presenting were again carried out three times, and the average results of the three tests are reported in Table 4, below (in the rows indicated "Wshd.").

TABLE 4

| Sample | Anti-Stat. Yarn | | Charge (kV) | Static-Influenced Agent Attached (%) | | | |
|---|---|---|---|---|---|---|---|
| | | | | Polyester Lint | Cotton Lint | Cat Hair | Dog Hair |
| 1 | 0% | Unw. | 5.3 | 0 | 0 | 0 | 0 |
| | | Wshd. | −12.6 | 83 | 0 | 100 | 67 |
| 2 | 0.65% | Unw. | +0.4 | 0 | 0 | 0 | 0 |
| | | Wshd. | −1.4 | 0 | 0 | 0 | 0 |
| 3 | 1% | Unw. | +0.5 | 0 | 0 | 0 | 0 |
| | | Wshd. | −1.1 | 0 | 0 | 0 | 0 |

The results illustrate that the presence of a fabric processing aid, such as a spin finish oil or coning oil, may temporarily reduce electrostatic attraction, e.g., by interfering the polarization. Although Sample 1 contains no anti-static yarn, it demonstrated no propensity to attract any static-influenced agents before washing. Upon washing, however, the fabric processing aid of Sample 1 was removed, and the washed sample demonstrated substantial propensity to attract polyester lint, cat hair, and dog hair. On the contrary, Samples 2 and 3, which comprised anti-static yarn, were unaffected by washing. Both before and after washing, Samples 2 and 3 demonstrate no propensity to attract any static-influenced agents. Thus, these differentiations can be used to determine the long-term effectiveness of anti-static means (e.g., fabric processing aid vs. anti-static yarn).

For example, using the disclosed testing method, it was quantitatively determined that Sample 1, which includes no anti-static yarn, demonstrates a much greater attraction propensity for polyester lint, cat hair, and dog hair after washing (83 vs. 0; 100 vs. 0; and 67 vs. 0, respectively). Furthermore, the testing method quantitatively determined that Samples 2 and 3, which include 0.65% and 1% of the anti-static yarn, respectively, demonstrate the same low attraction propensity for all four static-influenced agents before and after washing. Thus, the disclosed method demonstrates that the presence of the anti-static yarn may provide long-term effectiveness in reducing or eliminating the attraction propensity of the fabric.

In this way, the disclosed method may be utilized to quantitatively determine the long-term effectiveness of anti-static treatments.

Embodiments

Embodiment 1: An embodiment for measuring the attraction propensity of a fabric, the embodiment comprising the steps of charging a neutralized test fabric optionally by contacting with a charging fabric; presenting the charged test fabric a predetermined distance from a static-influenced agent such that at least a portion of the static-influenced agent attaches to the charged test fabric; and determining the quantity of attached static-influenced agent.

Embodiment 2: The embodiment of any of the preceding embodiments, wherein the charging comprises tribocharging the neutralized test fabric.

Embodiment 3: The embodiment of embodiment 2, wherein the tribocharged test fabric has an electric potential of greater than ±0 kV.

Embodiment 4: The embodiment of embodiment 2, wherein the tribocharging comprises rubbing the charging fabric along a surface of the neutralized test fabric at a speed from 1 in/s to 50 in/s.

Embodiment 5: The embodiment of any of the preceding embodiments, wherein the charged test fabric has an electric potential of greater than ±0 kV.

Embodiment 6: The embodiment of any of the preceding embodiments, wherein the static-influenced agent is present in a pre-measured amount.

Embodiment 7: The embodiment of any of the preceding embodiments, further comprising conditioning the neutralized test fabric and/or the charged test fabric to a controlled environment.

Embodiment 8: The embodiment of embodiment 7, wherein the controlled environment is maintained at a temperature from 10° C. to 30° C.

Embodiment 9: The embodiment of embodiment 7, wherein the controlled environment is maintained at a relative humidity from 0% to 70%.

Embodiment 10: The embodiment of embodiment 7, wherein the controlled environment is maintained at a relative humidity from 0% to 30%.

Embodiment 11: The embodiment of any of the preceding embodiments, wherein the charging comprises tumbling.

Embodiment 12: The embodiment of any of the preceding embodiments, wherein the predetermined distance is based on properties of the static-influenced agent.

Embodiment 13: The embodiment of any of the preceding embodiments, further comprising: neutralizing a base fabric to yield the neutralized test fabric.

Embodiment 14: The embodiment of embodiment 13, wherein the neutralizing comprises: washing and drying the test fabric; and conditioning the test fabric to the controlled environment.

Embodiment 15: The embodiment of embodiment 14, wherein the neutralizing further comprises: neutralizing the static charge of the test fabric.

Embodiment 16: The embodiment of any of the preceding embodiments, further comprising measuring the electric charge of the charged test fabric.

Embodiment 17: The embodiment of any of the preceding embodiments, wherein the test fabric comprises natural fibers, synthetic fibers of polyester, polyamide, polyalkene, or polyacrylic, composite fibers, woven or non-woven fabrics, laminate fabrics, combinations of natural and synthetic fibers, or blends thereof.

Embodiment 18: The embodiment of any of the preceding embodiments, wherein the charging fabric comprises natural fibers, synthetic fibers of polyester, polyamide, polyalkene, or polyacrylic, composite fibers, woven or non-woven fabrics, laminate fabrics, combinations of natural and synthetic fibers, or blends thereof.

Embodiment 19: The embodiment of any of the preceding embodiments, wherein the charging fabric comprises nylon-6,6, PET, wool, wool blends, nylon-cotton blends, or combinations thereof.

Embodiment 20: The embodiment of any of the preceding embodiments, wherein the static-influenced agent comprises polyester lint, cotton lint, human hair, cat hair, dog hair, dust, pollen, allergens, irritants, spores, or combinations thereof.

Embodiment 21: The embodiment of any of the preceding embodiments, wherein the predetermined distance is less than 5 inches.

Embodiment 22: The embodiment of any of the preceding embodiments, wherein the predetermined distance is less than 2 inches.

We claim:

1. A method for measuring the attraction propensity of a fabric, the method comprising the steps of:
   charging a neutralized test fabric by contacting with a charging fabric;
   presenting the charged test fabric a predetermined distance from a static-influenced agent such that at least a portion of the static-influenced agent attaches to the charged test fabric; and
   determining the quantity of attached static-influenced agent.

2. The method of claim 1 wherein the charging comprises tribocharging the neutralized test fabric.

3. The method of claim 2, wherein the tribocharged test fabric has an electric potential of greater than ±0 kV.

4. The method of claim 2, wherein the tribocharging comprises rubbing the charging fabric along a surface of the neutralized test fabric at a speed from 1 in/s to 50 in/s.

5. The method of claim 1, wherein the charged test fabric has an electric potential of greater than ±0 kV.

6. The method of claim 1, wherein the static-influenced agent is present in a pre-measured amount.

7. The method of claim 2, further comprising conditioning the neutralized test fabric and/or the charged test fabric to a controlled environment.

8. The method of claim 7, wherein the controlled environment is maintained at a temperature from 10° C. to 30° C.

9. The method of claim 7, wherein the controlled environment is maintained at a relative humidity from 0% to 70%.

10. The method of claim 7, wherein the controlled environment is maintained at a relative humidity from 0% to 30%.

11. The method of claim 1, wherein the charging comprises tumbling.

12. The method of claim 1, wherein the predetermined distance is based on properties of the static-influenced agent.

13. The method of claim 1, further comprising:
neutralizing a base fabric to yield a neutralized test fabric.

14. The method of claim 13, wherein the neutralizing comprises:
washing and drying the test fabric; and
conditioning the test fabric to the controlled environment.

15. The method of claim 14, wherein the neutralizing further comprises:
neutralizing the static charge of the test fabric.

16. The method of claim 1, further comprising measuring the electric charge of the charged test fabric.

17. The method of claim 1, wherein the test fabric comprises natural fibers, synthetic fibers of polyester, polyamide, polyalkene, or polyacrylic, composite fibers, woven or non-woven fabrics, laminate fabrics, combinations of natural and synthetic fibers, or blends thereof.

18. The method of claim 1, wherein the charging fabric comprises natural fibers, synthetic fibers of polyester, polyamide, polyalkene, or polyacrylic, composite fibers, woven or non-woven fabrics, laminate fabrics, combinations of natural and synthetic fibers, or blends thereof.

19. The method of claim 1, wherein the charging fabric comprises nylon-6,6, PET, wool, wool blends, nylon-cotton blends, or combinations thereof.

20. The method of claim 1, wherein the static-influenced agent comprises polyester lint, cotton lint, human hair, cat hair, dog hair, dust, pollen, allergens, irritants, spores, or combinations thereof.

21. The method of claim 1, wherein the predetermined distance is less than 5 inches.

22. The method of claim 1, wherein the predetermined distance is less than 2 inches.

* * * * *